(12) United States Patent
Belongia et al.

(10) Patent No.: US 7,228,992 B2
(45) Date of Patent: Jun. 12, 2007

(54) FLUID DISPENSER CARTRIDGE

(75) Inventors: Brett M. Belongia, North Andover, MA (US); Stephen P. Proulx, Boxborough, MA (US)

(73) Assignee: Millipore Corporation, Billerica, MA (US)

( * ) Notice: Subject to any disclaimer, the term of this patent is extended or adjusted under 35 U.S.C. 154(b) by 277 days.

(21) Appl. No.: 10/635,124

(22) Filed: Aug. 6, 2003

(65) Prior Publication Data

US 2005/0029301 A1 Feb. 10, 2005

(51) Int. Cl.
  *B67D 5/58* (2006.01)
(52) U.S. Cl. ................... 222/189.09; 137/587
(58) Field of Classification Search ........... 222/189.09; 137/587
  See application file for complete search history.

(56) References Cited

U.S. PATENT DOCUMENTS

| | | | | |
|---|---|---|---|---|
| 5,203,367 A | | 4/1993 | Akai et al. ............. | 137/101.25 |
| 5,464,127 A | * | 11/1995 | Burrows .................. | 222/185.1 |
| 5,480,063 A | | 1/1996 | Keyes et al. ................... | 222/64 |
| 5,586,586 A | * | 12/1996 | Fiech ............................ | 141/98 |
| 5,680,960 A | | 10/1997 | Keyes et al. .................. | 222/64 |
| 5,848,326 A | * | 12/1998 | Komuro et al. ................ | 399/98 |
| 5,971,009 A | * | 10/1999 | Schuetz et al. ............. | 137/312 |
| 6,073,812 A | * | 6/2000 | Wade et al. ........... | 222/189.09 |
| 6,554,881 B1 | * | 4/2003 | Healey ........................ | 55/528 |
| 6,793,102 B2 | * | 9/2004 | Tan et al. ................ | 222/185.1 |
| 2004/0194831 A1 | * | 10/2004 | Balsdon ...................... | 137/587 |

OTHER PUBLICATIONS

"Acerta Disposable Filing System", Millipore Corporation Product Brochure (Dec. 2002).

* cited by examiner

*Primary Examiner*—J. Casimer Jacyna

(57) ABSTRACT

A single-use fluid dispenser cartridge, installable or installed into a host fluid dispensing apparatus, is described. The single-use fluid dispenser cartridge is provided with a fluid reservoir, a fill tube assembly, and means for controlling pressure within the cartridge by gating gas into or out of the reservoir and/or the fill tube assembly. The gas gating mean enables, in certain embodiments, use of a fluid reservoir that is "substantially rigid".

22 Claims, 2 Drawing Sheets

FLUID DISPENSER CARTRIDGE

FIELD

The present invention relates in general to fluid dispensing, and particularly, to a single-use fluid dispenser cartridge installed or installable within a host fluid dispensing apparatus, the cartridge having a substantially rigid fluid reservoir, a fill-tube assembly, and means for affecting internal pressure within the cartridge.

BACKGROUND

Numerous types of fluid dispensing apparatuses exist for filling bottles. One type of fluid dispensing apparatus which is in widespread use is positive displacement fillers. Positive displacement fillers typically include moving parts which contact and displace the fluid being dispensed. For example, one type of positive displacement filler uses a piston and cylinder arrangement. In this type of positive displacement filler, the backward movement of the piston draws fluid into the cylinder through an inlet port and the forward movement of the piston expels the fluid through an outlet port. Another type of positive displacement filler uses a rotary pump to move the fluid.

Positive displacement pumps have gained widespread use in the United States for two reasons. First, positive displacement pumps can operate at relatively high speeds, filling as many as six hundred bottles per minute. Additionally, positive displacement pumps are accurate up to about ±0.5%.

Despite the widespread use of positive displacement fillers, they nevertheless have several disadvantages. One disadvantage with positive displacement fillers is that the fluid comes into contact with moving parts. As the moving parts wear, particulate matter enters the fluid causing particulate contamination. If severe enough, particulate contamination can render the product unusable. Another disadvantage with positive displacement fillers involves the difficulty in cleaning and sterilizing the moving parts in contact with the fluid. In positive displacement pumps, the critical tolerances between pads, such as the piston and cylinder, precludes effective cleaning in place. Thus, the user must disassemble the apparatus for cleaning and sterilization. This process is not only time consuming, but may result in biological contamination of the pads when they are handled by the mechanic during re-assembly.

Another type of fluid dispensing apparatus is the time/pressure filler. Generally speaking, the time/pressure filler includes a fluid reservoir which is maintained under a relatively constant pressure. The fluid is dispensed from the reservoir through a compressible line. Fluid flow is shut off by a pinch type valve which squeezes and collapses the discharge line. A pre-determined volume of fluid is dispensed by opening the discharge line for a pre-determined period of time and then closing the line. If the pressure within the fluid reservoir is maintained constant, an equal amount of fluid should be dispensed each time the cycle is repeated. However, time/pressure fillers do not work as well in practice as they do in theory.

Another type of fluid dispensing apparatus is shown in U.S. Pat. No. 5,090,594 which discloses a volumetric fluid dispensing apparatus. The volumetric dispensing apparatus measures a predetermined volume of fluid in a measuring cup or fill tube which is subsequently dispensed into a receptacle. Volumetric fillers, while slower than positive displacement fillers, are highly accurate and avoid the problems of microbial and particulate contamination. However, volumetric fillers, like time/pressure fillers, depend on a relatively constant pressure. For this reason, it is impractical to use clarification filters in volumetric fillers since the pressure drop across the filter may result in inaccurate filling.

Another type of fluid dispensing apparatus is described in U.S. Pat. No. 5,480,063, issued to Keyes et al. on Jan. 2, 1996. Keyes et al. describe an apparatus having no moving parts in contact with the fluid being dispensed. The fluid-dispensing apparatus includes a fluid chamber containing the fluid to be dispensed and a fill tube communicatively connected to the fluid chamber. The fill tube forms a circuit with the fluid reservoir. In operation, fluid is transferred from the chamber into the fill tube. When the fluid level in the fill tube reaches a predetermined height, filling is terminated and fluid dispensed from the fill tube into a container. See also, U.S. Pat. No. 5,680,960, issued to Keyes et al., on Oct. 28, 1997.

Despite the approaches embodied in the aforementioned patents, there is a continuing need for improvements to and/or alternative configurations for fluid dispensing apparatuses, particularly those implementing disposable single-use, fluid handling components.

SUMMARY

In response to the above need, the present invention provides a novel fluid dispenser cartridge suitable for installation into a host apparatus for dispensing predetermined volumes of fluid. The fluid dispenser cartridge—being particularly well suited to manufacture in single-use format—comprises, in a principal embodiment, a substantially rigid fluid reservoir, a fill tube assembly, and means for gating gas into or out of the substantially rigid fluid reservoir or the fill tube assembly.

More particularly, the substantially rigid fluid reservoir is provided with a fluid inlet and a fluid outlet, the fluid inlet suitable for introducing fluid into the substantially rigid fluid reservoir, the fluid outlet suitable for releasing said fluid. The fill tube assembly is connected at the fluid outlet to the substantially rigid fluid reservoir such that fluid from said substantially rigid fluid reservoir can flow into said fill tube assembly. The fluid within the fill tube assembly is dispensed therefrom through a discharge port provided therein for that purpose. The fluid dispenser cartridge is physically robust and durable, allowing for use in a comparatively broad range of environments, while promoting accurate, fast, easy, and economical fluid dispensation.

Although the means for gating gas, in respect of certain embodiments of the present invention, enable and/or otherwise allow for effective use of a fluid reservoir that is "substantially rigid", other embodiments are contemplated. For example, advantage can be derived from a fluid dispenser cartridge wherein said gas gating means is essentially a gas permeable patch provided on a substantially non-rigid fluid reservoir.

In light of the above, it is a principal object of the present invention to provide a durable single-use fluid dispenser cartridge installed or installable into a host fluid dispensing apparatus.

It is another object of the present invention to provide a single-use, fluid dispenser cartridge installed or installable into a host fluid dispensing apparatus, said fluid dispenser cartridge comprising, in unitary construction, a fluid reservoir, a fill tube assembly, and means for gating gas into or out of either the reservoir or the fill tube assembly.

It is another object of the present invention to provide a fluid dispensing apparatus having and/or implementing both a substantially rigid fluid reservoir connected to a fill tube assembly and means for gating gas into and out of either the reservoir or the fill tube assembly.

It is another object of the present invention to provide a single-use fluid dispenser cartridge, installable into a fluid dispensing apparatus, comprising means for maintaining pressure equilibrium within said cartridge during use thereof.

It is another object of the present invention to provide an open-loop single-use fluid dispenser cartridge, installable into a fluid dispensing apparatus, comprising a substantially rigid fluid reservoir and means for maintaining pressure equilibrium within said cartridge during use thereof.

With these and other objects in view which will more readily appear as the nature of the invention is better understood, the invention subsists in its novel combination and assembly of parts hereinafter more fully described and claimed.

DETAILED DESCRIPTION

Figure 1:
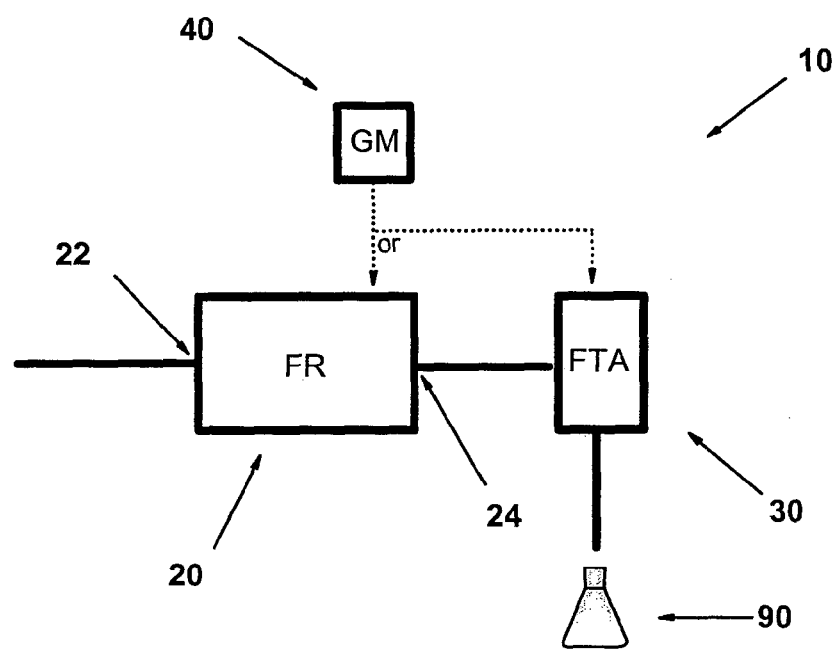
FIG. 1 is a schematic representation of a fluid dispenser cartridge 10 according to the present invention.

The present invention provides a novel means for dispensing fluids, particularly fluids used for or resulting from biopharmaceutical or pharmaceutical manufacturing processes. These means are preferably embodied as a fluid dispenser cartridge 10 that is either installed (i.e., a fixed cartridge) or installable (i.e., a disposable, single-use cartridge) into a host fluid dispensing apparatus. As shown in FIG. 1, the fluid dispenser cartridge 10 employs a reservoir 20 and a fill tube assembly 30. Fluid is dispensed into a receptacle 90 most immediately from the fill tube assembly 30, the fluid content thereof being replenished after each dispensation by flowing controlled dosages thereinto from the reservoir 20.

The single-use fluid dispenser cartridge 10 is particularly characterized by the use therein of means 40 for gating gas in or out of the cartridge 10, for example, to provide the appropriate pressure differential among the components (20 and 30) of the cartridge 10 that yields accurate, repeatable fluid dispensation. The gas gating means 40 are preferably configured to allow the transit of gas therethrough, while substantially blocking (or otherwise frustrating) transit of other matter. With such gas gating mean 40, the fluid dispenser cartridge can—among other things—more effectively utilize a fluid reservoir that is "substantially rigid".

A fluid dispensing apparatus—when fitted with a fluid dispenser cartridge 10 according to the present invention—is well suited, for example, for dispensing precisely and consistently into a container (or containers) measured volumes (or individual dosages) of fluid. Since the fluid dispenser cartridge can be configured easily as a hermetic or otherwise sanitary enclosure, the fluid dispensing apparatus is particularly amenable to pharmaceutical applications. In this and other uses, the apparatus can provide advantage in respect of its accuracy (i.e., the apparatus has an accuracy comparable to positive displacement pump systems); ease of operation (e.g., the apparatus does not require mechanical calibration); suitability for use in a clean room (i.e., the apparatus can be designed with few particle-shedding moving parts); and low maintenance (cf., uses a single-use disposable cartridge).

A host fluid dispensing apparatus will typically comprise essentially all the "fixed" mechanical and electronic means (e.g., plumbing, circuitry, wiring, energy source, pumps, support structures, manifolds, valves, supply or other supplemental fluid reservoir, logic chips, and like subcomponents) that enable a fluid to be brought into single-use fluid dispenser cartridge 10 and dispensed therefrom.

The host fluid dispensing apparatus can vary considerably in its overall configuration and in its collection of subcomponents, but its basic functionality of "operating" the disposable cartridge remain the same throughout. Typically, the mechanical and electronic means forming collectively the host fluid dispensing apparatus will be contained in generally fixed arrangement within a rigid outer housing or cabinet. Further details and examples of host fluid dispensing apparatuses can be found in U.S. Pat. Nos. 5,480,063 and 5,680,960, issued to Denis E. Keyes et al. on Jan. 2, 1996 and Oct. 8, 1997, respectively.

The fluid dispensing cartridge 10 is preferably made as a "single use" item. In this regard, it is "single-use" in the sense that at the completion of a fluid dispensing operation, the component can be either disposed (as is sometime required by law after dispensing certain environmentally-regulated substances) or recycled (e.g., after dispensing non-regulated substances).

Figure 2:
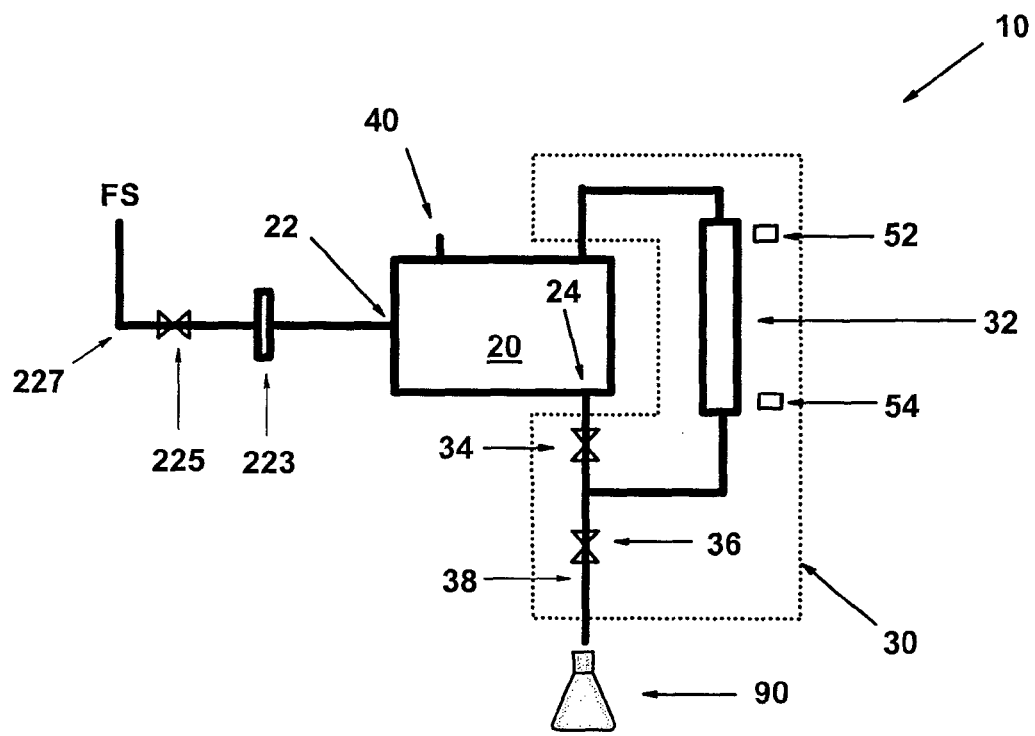
FIG. 2 is a single-use fluid dispenser cartridge 10 according to a "closed loop" embodiment of the present invention.
Figure 3:
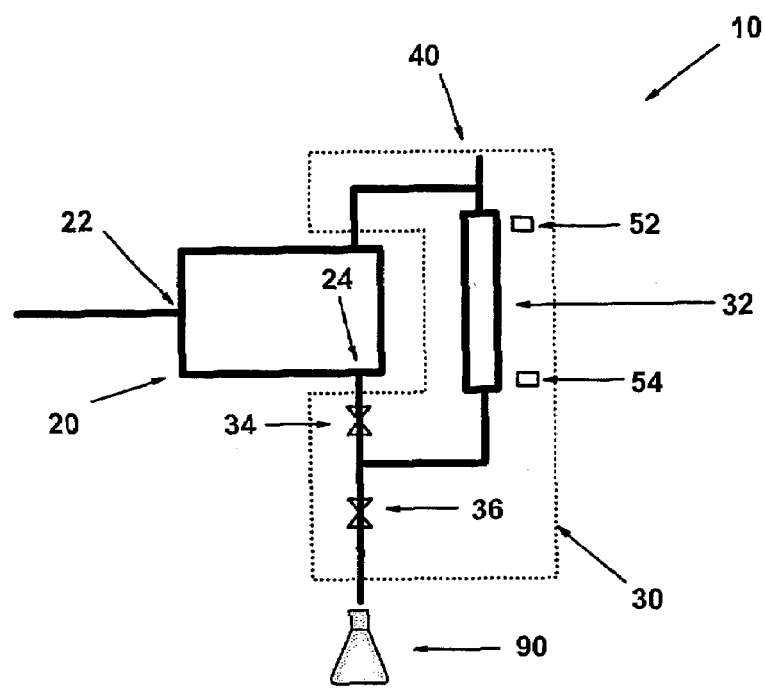
FIG. 3 is a single-use fluid dispenser cartridge 10 according to another "closed loop" embodiment of the present invention.
Figure 4:
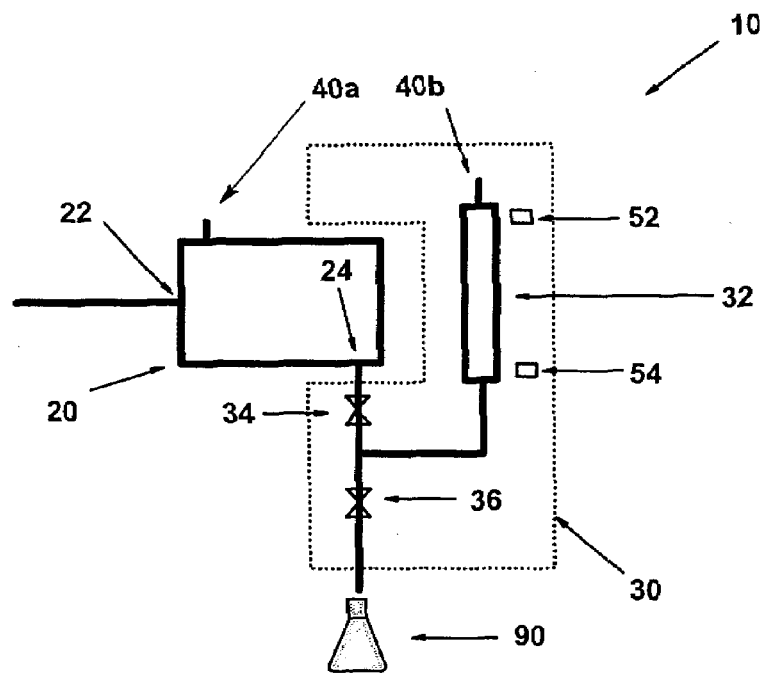
FIG. 4 is a single use fluid dispenser cartridge 10 according to a "non-closed loop" embodiment of the present invention.

The "consumable" fluid dispenser cartridge 10 of the present invention has -- as shown in FIGS. 2 to 4 -- several embodiments. However, certain components are present in all embodiments. In particular, the fluid dispenser cartridge 10 in all its embodiments will have: (a) a fluid reservoir 20 having a fluid inlet 22 and a fluid outlet 24, the fluid inlet suitable for introducing fluid into the fluid reservoir, the fluid outlet suitable for releasing fluid from said fluid reservoir; (b) a fill tube assembly 30 connected to the fluid reservoir's fluid outlet such that fluid from the fluid reservoir can flow into said fill tube assembly, the fill tube assembly having a discharge port for dispensing fluid out of said fill tube assembly; and (c) the aforementioned means for gating gas 40 into or out of either the fluid reservoir 20 and/or the fill tube assembly 30.

In FIG. 2, the fluid dispenser cartridge includes a substantially rigid fluid reservoir 20 having a fill port 22 (i.e., a fluid inlet) connected by a fluid supply line 227 to a fluid source FS. A sterilization or clarification filter 223 is typically disposed in the fluid supply line. The fluid supply line 227 includes a supply valve 225 activatable, for example, by a solenoid, or other functionally equivalent device or mechanism.

The fluid reservoir 20 includes a drain port 24 (i.e., a fluid outlet) connected to a lower end of fill tube assembly 30. Another end of fill tube assembly 30 is connected to an opening in the upper portion of the fluid reservoir 20. Thus, as shown in FIGS. 2 and 3 the fill tube assembly 30 forms a closed loop with the fluid reservoir 20. (Cf., FIG. 4).

When the filter dispenser cartridge 10 is installed into a host fluid dispensing apparatus, a fill valve 34 (e.g., a pinch valve) within the host is operatively engaged onto the fill tube assembly to control the flow of fluid from the fluid reservoir 20 to the fill tube assembly 30. The fill valve 34 is, in certain embodiments, controlled by a solenoid connected to a programmable controller (found also within the host). Other well-known valve control devices or mechanisms or systems can be employed.

A drain line 38 (i.e., a discharge port) is provided in the fill tube assembly 30 for dispensing fluid from the fill tube assembly 30 into a container 90. When the filter dispenser cartridge 10 is installed into a host fluid dispensing apparatus, a drain valve 36 (e.g., a pinch valve) within the host is operatively engaged onto the fill tube assembly to control the flow of fluid from the fill tube assembly 30 to a container 90. The drain valve 36 is, in certain embodiments, controlled by a solenoid connected to the programmable controller. Again, other well-known valve control devices or mechanisms or systems can be employed.

Although in FIG. 2, the discharge port 38 is provided by a conduit leading off the closed loop of the fill tube assembly 30, other structures are contemplated. For example, in embodiments wherein the fill tube assembly does not form a closed loop with the reservoir, the discharge port may simply be a controllable opening at the downstream end of the fill tube assembly. Regardless, whether closed or not, for pharmaceutical applications, the discharge end of the fill tube assembly is preferably fitted, for example, with a hermetically-enclosed syringe needle to enable aseptic fluid dispensation.

When the fluid dispenser cartridge is installed into a host fluid dispensing apparatus, optical fluid level sensors 52 and 54—provided by said host—are operatively engaged along the fill tube assembly's measuring tube 32. When fill valve 34 is "opened" and discharge valve 36 "closed", fluid flows out of the fluid reservoir, ultimately into the measuring tube 32. The optical fluid level sensors are used to monitor the progress of such "filling", thus providing means for the control thereof. As described in greater detail below, the optical fluid level sensors 52 and 54 can be replaced, if desired, by electroconductive capacitance-based sensors. Other fluid level sensors, such as electronic, electrooptical, electrochemical, and sonic sensors, can also be used.

In one mode of practice, a programmable controller (not shown)—or other electronic logic device or system—is operatively connected to the fluid level sensor 52 and 54. When the fluid level in the fill tube assembly 30 reaches certain predetermined upper or lower limits (as detected by the sensors), the programmable controller (or said other system) signals the valves 34 and 36 to "open" or "close", allowing more fluid into the fill tube assembly 30 or discharging it therefrom, depending on what is desired. If desired, multiple optical sensors can be used to several define upper, lower, and intermediate limits.

The embodiment illustrated in FIG. 3 bears similarities to the embodiment illustrated in FIG. 2. However, whereas the gas gating means 40 in FIG. 2 is disposed on the reservoir 20, in the embodiment of FIG. 3 the gas gating means 40 is disposed within the fill tube assembly 30. Since the fluid levels in the fill tube assembly 30 and fluid reservoir 20 in both the FIG. 2 and FIG. 3 embodiments are unlikely to rise up into the upper reaches of these components (20 and 30), there will typically exist a continuity in the enclosed space therebetween. To a certain extent, there are no particular limitations that will dictate the specific point along such continuous region at which one can or should provide the gas gate means 40. Placement either on the fluid reservoir 20, or the fill tube assembly 30, or both is possible. Considering however that the fluid reservoir 20 will in most circumstances have a larger surface area than the fill tube assembly 30, it may be more practical from a manufacturing standpoint to place the gas gating means 40 thereon. This of course will not necessarily always be the case.

Latitude in the placement of the gas gating means is comparatively more constricted in the embodiment shown in FIG. 4. Unlike the embodiments of FIGS. 2 and 3, the fluid dispenser cartridge 10 shown in FIG. 4 is not a "closed loop". In such "non-closed loop" configurations, spaces above the expected predetermined fluid levels in both the substantially rigid reservoir 20 and the fill tube assembly 30 are separate and distinct. To maintain, steady head pressure for fluid dispensation, it is desirable to ensure that the atmospheric pressure above the fluid in the reservoir 20 and in the fill tube assembly 30 are substantially equal. Gas gating means 40a and 40b are thus preferably provided on both the fluid reservoir 20 and the fill tube assembly 30. This allows gas to flow aseptically into and out of both components, thus equalizing the pressure therein to that of the outside ambient environment.

It will be appreciated that the use of more than one set of gas gating means is not limited to non-closed loop embodiments. In a closed loop systems, for example, it is contemplated that devices or structures (e.g., valve, sensors, and the like) may be installed within the fill tube assembly's return line back to the reservoir, thus breaking or otherwise interrupting the continuity of the enclosed space therebetween. In such situations, it may be desirable to vent the enclosed spaces before and after the break in continuity.

Among its several functions, the substantially rigid reservoir is used to store the fluid. It's relative size, location, and positioning within the system is selected to provide—in combination with the influence of the gas gating means—the appropriate degree of so-called "head pressure" necessary to run the system. This is generally a function of its height in comparison with the height of the integrated fill tube assembly.

As indicated, in accordance with the present invention, the reservoir is either completely rigid in structure, or is provided with rigid side walls. The typical embodiment is configured as a molded (or otherwise shaped), single-piece (or otherwise unitary) so-called "hard-shell" bag. The reservoir may initially be made in two-halves, with a subsequent assembly operation rendering the halves into a single unitary piece. Alternatively, the reservoir can be blow-molded from, for example, polyethylene terephthalate. Other methods exist.

By indicating that the reservoir or its side walls are rigid, it is not intended that the invention be narrowly limited to absolute and unyielding rigidity. Those skilled in the art will in light of the present disclosure understand the scope of the tem "substantially rigid". A substantially rigid reservoir, for example, will resist but nonetheless yield to external forces substantially greater than the forces exerted by normal ambient atmospheric pressure. It will still be considered "substantially rigid" if it retain its shape when filled with fluid to its predetermined maximum capacity; or—if it does not retain its shape—if it comprises rigid side wall.

Examples of materials useful for the manufacture of the substantially rigid fluid reservoir, and/or its rigid side walls, include polyethylene terephthalate, high density polyethylene, polyvinyl chloride, polypropylene, and polystyrene. Materials aside from polymeric ones such as metal (e.g., aluminum) and glass (e.g., fiberglass composites) can also be considered. In respect of polymeric materials, examples of manufacturing processes therefor include injection molding, compression molding, transfer molding, blow molding, and extrusion. These processes can of course be used for making the substantially rigid fluid reservoir, or parts thereof, for later assemblage.

For example, thermoset polymers affording high rigidity can be employed for devices intended for use in elevated temperature conditions. Such elevated temperatures could occur, for example, in working with viscous substances, the dispensation thereof being conducted at a temperatures allowing better flow, such as ointments, and the like.

As another embodiment, it is envisioned that the substantially rigid fluid reservoir can be configured as a molded plastic container, into which is contained the unassembled components of the single-used fluid dispenser cartridge. The reservoir thus essentially functions dually as a fluid tank (in use) and as packaging (in commercialization). This design is likely not suitable for many sterile applications, as the components still have to be assembled prior to use, thus calling for users of comparatively high technical expertise. But, for applications that require accurate small volume dispensation of fluids intended for non-pharmaceutical and non-clinical use—areas that are not categorically excluded by the present invention—the rigidity of the reservoir provides advantage in respect of such a packaging scheme owing to the greater durability thereof.

As an alternative to being completely rigid, it is envisioned that the reservoir comprise a series of rigid side-walls that bend or flex along folds or creases or crumple zones, and the like, such that the reservoir is capable of collapsing, or otherwise, diminishing its volume. Such configuration provides both operative pressure-related advantages, as well as saves space in respect of storage of the consumable. Several collapsible configurations are envisioned, such as accordion-like configurations, bellows-like configurations, and configurations having pleated side-walls.

In the interest of reducing manufacturing costs, the substantially rigid fluid reservoir is preferably of substantially unitary construction. In particular, the substantially rigid fluid reservoir has minimal assembled parts and sub-components, and generally comprises a uni-layer construction.

In conducting fluid dispensation with the inventive apparatus, the maintenance of appropriate internal pressure conditions is important. As fluid moves from the substantially rigid fluid reservoir, to the fill tube assembly, and out of the apparatus into a receptacle, gas pressure within the substantially rigid reservoir and fill tube assembly can fluctuate if not controlled, and thus lead to inaccuracies in dispensed volumes, which is unacceptable, for example, when the product dispensed is to be an accurate dosage of pharmaceutical product. In the present invention, appropriate internal pressure conditions are promoted by the installation of the aforementioned gas gating means to maintain atmospheric pressure throughout the assembly.

The structure, location, and configuration of the gating means is subject to variation, depending on such factors as, intended application and reservoir and fill tube assembly structure, such as their internal dimensions, and the number of heads in the fill tube assembly. Two principal embodiments, however, are a vent filter assemblage and a pressure activated valve. Of these two mechanisms, the vent filter in consideration of its potentially lower implementation costs is particularly preferred.

In respect of the vent filter assemblage, a representative embodiment comprises a structure molded into or installed onto the fill tube assembly or the substantially rigid fluid reservoir that forms thereon an inlet and an outlet, with a passage therebetween, and a membrane or filter cross-sectionally dividing said passage.

There are no particular limitations to the type of membrane or filter employed for the vent filter assemblage. One can employ, for example, depth filters, surface filters, membranes, potted hollow fiber membranes, and the like. However, in view of the likely applications of the apparatus, hydrophobic filters or membranes are preferred inasmuch as such hydrophobicity would prevent release of aqueous fluid from the apparatus, yet allow gas to pass freely therethrough. The porosity of the filter or membrane should be selected to maintain aseptic condition and prevent contamination of the fluid, for example, by airborne particles and the like from the external ambient environment. Membranes having both hydrophobic and hydrophilic functionalities may also employed. Details of such multi-functional vent filters are described in PCT International Application Pub. No. WO 02/043,841, filed by J. Cappia et al. on Dec. 3, 2001.

The structure of the vent filter need not be overly complicated. In the interest of disposability (cf., single-use), structures capable of low manufacturing costs—such as those not requiring extensive assembly, or have a low number of parts, or utilizing commercially available commodity materials—provide certain advantages. One type of vent filter that can be implemented with little cost would be to provide a discrete dedicated zone within the single-use cartridge that comprises a substantially-gas permeable fluoropolymer membrane (e.g., "Gore-Tex"-brand membrane commercially available from Gore, Inc. of Wilmington, Del.) or a substantially gas permeable sheet of polyethylene fiber (e.g., "Tyvek"-brand material commercially available from E. I. du Pont de Nemours, Inc. of Wilmington, Del. In one embodiment, an opening is provided in the reservoir (e.g., by cutting, stamping, or pre-made) in an area above the reservoir's highest intended fluid fill level, followed by closing said opening with the porous sheet polymer. In this embodiment, the porous patch can be fixed in place by adhesives or other bonding compositions; or sonically welded, sintered, fused, taped, or caulked. In the same manner as its use in the reservoir, the patch can also be used in the fill tube assembly—again, in an area above fill tube assembly's predetermined highest fluid level.

In respect of the pressure-activated valve, a desirable embodiment would be one that operates automatically in response to pressure fluctuations within the apparatus. This could occur either electronically or mechanically. In respect of mechanical means, a valve can be configured that has one position below a certain pressure, and another position when the pressure rises above that pressure. Where greater accuracy and sensitivity is required, an electronic valve system can be implemented together with sensors. Such electronic valve system can be controlled through the electronic controller of the host apparatus. Further, since it is likely that electronic valves will be costly (hence, not easily disposable), the single-use fluid dispenser cartridge can be made only to provide means for connection (i.e., a tube) to an electronic valve system installed as a permanent fixture to fixed hardware of the host fluid dispensing apparatus.

The operation of a fluid dispensing apparatus having installed therein a fluid dispenser cartridge 10 commences with the loading of the fluid reservoir with the fluid for dispensation, this fluid typically being held initially in the fluid supply FS of the host apparatus. Loading is accomplished by "opening" or otherwise rendering accessible the fluid inlet into the fluid reservoir, for example, by "opening" supply valve 225. At this point, the fill valve 34 proximate the fluid output end 24 of the fluid reservoir 20 is "closed".

After loading the reservoir 20, the means by which fluid is introduced into the reservoir is also then "closed".

The next step involves loading the fill tube assembly 30—in particular, the sight tube 32—with fluid from the reservoir 20. This is accomplished by opening the fill valve 34, while keeping the drain valve 36 "closed". When fluid gradually flows into the fill tube assembly from the substantially rigid reservoir, its level therein is monitored by the fluid level sensors, the data thereof being processed by an electronic control system. Once a certain fluid level is reached, indicative of a desired volume, the fill valve 34 is "closed".

The next step involves dispensing the fluid from the fill tube assembly 30 into a vial 90 or other container. This is accomplished by "opening" the drain valve 36 provided in the discharge tube 38, emptying substantially the fluid content of the fill tube assembly 30. Because the internal dimensions of the fill tube assembly 30, and the properties of the fluid and its viscosity, are known beforehand, the amount of fluid that drains outs of the fill tube assembly 30 can be predetermined with a good degree of accuracy. The use of gas gating means, as taught herein, contributes to and assure such accuracy.

It will be appreciated that the present invention does not require all fluid to drain out of the fill tube assembly. In fact, certain fill tube assembly configurations may be designed specifically to retain some volume of fluid. But again, since this is know beforehand, it can be factored into the control mechanisms, and thus not compromise dispense accuracy.

Although not a limit to the present invention, in respect of the dispensing of pharmaceutical fluids, the typical total internal volume of a fluid reservoir tends to be in the range of about 1.5 liters to about 10 liters. With such volumes, the dimensions of the supply inlet, vent outlet, and fluid output are as follows: The diameter of the supply inlet ranges from about 0.25 inch to about 0.75 inch (about 0.635 cm to about 1.90 cm); the diameter of the vent outlet ranges from about 0.125 inch to about 0.75 inch (about 0.3175 cm to about 1.90 cm); and the diameter of the fluid outlet ranges from about 0.125 inch to about 0.75 inch (about 0.3175 cm to about 0.1.90 cm). For greater volumes—particularly, when involving viscous fluids—these dimensions will be substantially larger.

In respect of the fill tube assembly, a preferred configuration for the sight tube 32 is one having tapered inside walls which taper outwardly from a vertical center line in a direction from a lower portion of the sight tube to an upper portion of the sight tube. The angle between the central vertical axis and the inclined wall is between about 1 to 10 degrees, preferably about 2 and 4 degrees.

A tapered sight tube provides a number of advantages over a sight tube having a constant inner diameter. Since the sight tubes are filled with fluid from the reservoir, the fluid level in the sight tube 32 can not without further intervention rise above the fluid level in the reservoir. Hence, assume equal inner diameters at one of their ends, a tapered sight tube enables a greater volume of fluid to be filled therein than a constant inner diameter tuber. Furthermore, with a sight tubes of varying diameter over a given length, the fluid travels a shorter vertical distance as compared to the same fluid in a constant diameter tube. Since the fluid in a varying diameter tube travels a shorter distance and velocity for a given volume, a lower pressure drop results and greater control over dispensation is affected.

As mentioned, since the fluid dispenser cartridge is likely to be discarded after use, advantage is gained by assuring that the materials in this consumable component are off modest value. In this regard, it will be understood that comparatively costly sub-components—such as valves and complex and/or sophisticated electronic components—will likely not be part of the cartridge, but rather fixtures of the host fluid dispensing apparatus. With regard to the aforementioned drain valve and fill valves, these will likely, but not necessarily, be of the pinch-type variety, mounted within the assembly hardware. When a fluid dispenser cartridge is installed, specific regions of its fill tube assembly will be united with this valve (e.g., clipped into) such that their functionality can be realized. Pinch valves—in this light— can be seen as advantageous in that they don't require any cutting of tubes and mating of valve elements—a task requiring some measure of technical proficiency. Rather, the specific regions of the tube only be sufficiently "pinchable", to permit the pinch valves to clamp down on the region sufficiently to collapse and shut the lumen of the tube. In this manner, the valves need not necessarily be part of the disposable element.

In order to determine the fluid level in the fill tube assembly, a pair of optical sensors are disposed along the fill tube assembly. Both sensors should be disposed below the level of the fluid in the fluid chamber. The upper level sensor defines an upper level of the fluid in the fill tube. The lower level sensor defines a lower level of fluid. The volume of fluid dispensed between the upper and lower level sensors, the diameter of the fill tube, and the so-called "head pressure". Both sensors are connected to a programmable connector or other electronic logic device.

A meniscus sensor may be included in addition to or in place of the level sensors. If a meniscus sensor is used, it is located in a tube extension in the fill-tube loop. The meniscus sensor is a laser-type sensor which measures the height of the meniscus in the filled tube. The output of the meniscus sensor can be, for example, transmitted to a programmable controller which uses the information to improve the accuracy of the fill volume.

As indicated above, the fluid level in the fill tube assembly can also be monitored using—instead of optical fluid level sensors 52 and 54—capacitance sensors. Such sensors are preferably used on the fill tube assembly, but possibly also installed in the substantially rigid reservoir.

The electroconductive terminal by themselves are not sufficient to render operable the fluid dispensing apparatus. The electroconductive terminals need to be wired or otherwise linked or connected to both an energy source and an electronic control mechanism, both of which can be integrated as a single sub-component. The energy source essentially drives a current through both terminals, whilst the electronic control mechanism—for example, by incorporation therein of a potentiometer or like electronic sensor— measures the capacitance of said current and, based thereon, selectively opens and/or closes the fill valve and/or the discharge valve.

The electronic circuitry enabling the capacitance detection should also be configured with an eye towards economy. Thus, for example, the consumable fluid dispenser cartridge includes the terminals, and perhaps some leads and wires, that are plugged into and/or otherwise connected to appropriate dedicated sockets into the controller mechanism of the assembly, which is part of the non-disposable hardware assembly of the host apparatus.

The electronic terminals preferably comprise two narrow metal strips, typically copper, that can be mounted permanently to the side wall of the fill tube assembly. In a typical configuration, the strips are mounted opposed to one another on the outside of the tube and traverse the entire working length of the "sighting region" of the fill tube assembly. Capacitance detection is accomplished by passing a pulsed current across the space between the two metal strips. The capacitance of the material separating the strips is measured. There is a significant difference between the capacitance of an empty air-filled tube and one that is liquid filled. Therefore, the liquid volume can be continually monitored as it move up and down the tubing. In certain instances, the temperature will also have to be known, as it does have an effect on capacitance.

Alternatives exist to the placement of the copper strips on the outside surface of the fill tube assembly. For example, the copper strips can be mounted as follows: One is mounted on the outside of the tube (perhaps towards a bottom portion thereof) and the second is placed inside the fill tube assembly suspended without touching the walls. This version is particularly appropriate for high viscosity fluids that tend to "cling" vigorously to the tube's side walls. To prevent unwanted chemical interaction between the internally mounted terminal and fluid loaded into the fill tube assembly, the internally mounted terminal is preferably coated with a chemically non-reactive polymeric material or otherwise protected or isolated with some other suitable barrier.

In the operation of the host fluid dispensing apparatus, the capacitance in the fill tube assembly is measured continuously, so that the volume of in the tube will be continuously determined, rather than determining certain minimum and maximum volumes. Since the capacitance sensor measures the liquid continuously, so-called "proportional-integral-derivative" (PID) control of the system, rather than only proportional control, can be used thus improving the dispense accuracy and the repeatability.

Based on the foregoing, it is apparent that the present invention enables a fluid dispensing apparatus in which all of the components which come in contact with the fluid being dispensed can be pre-cleaned and sterilized. These components can be easily and quickly replaced thereby eliminating so-called maintenance "down time". The present invention also may be used with clarification filters without the errors associated with prior art devices.

While several embodiments are disclosed herein, those skilled in the art, having the benefit of the teaching set forth herein, can effect numerous modifications thereto. For example, the embodiments of the present invention illustrated in the Figures—discussed further below—all show a single fill tube assembly per reservoir. In practice, however, it is more advantageous to use several fill tubes assemblies per reservoir. The basic configuration and function of such additional fill tube assemblies will essentially be the same as that described above. These and other modifications are intended to be within the scope of the present invention as set forth in the appended claims.

The invention claimed is:

1. A fluid dispenser cartridge suitable for installation into an apparatus for dispensing predetermined volumes of fluid, the fluid dispenser cartridge comprising:
   a fluid reservoir having a fluid inlet and a fluid outlet, the fluid inlet suitable for introducing fluid into the fluid reservoir, the fluid outlet suitable for releasing fluid from the fluid reservoir;
   a fill tube assembly connected to said fluid reservoir at said fluid outlet such that fluid from said fluid reservoir can flow into said fill tube assembly during use of said cartridge in said apparatus, the fill tube assembly having a discharge port for dispensing fluid out of said fill tube assembly and having a measuring tube suitable for measuring a desired volume; and
   means for gating gas into or out of either said fluid reservoir or said fill tube assembly to substantially equalize pressure to that of the ambient environment during use of said cartridge in said apparatus; said gas gating means being disposed in either said fluid reservoir or said fill tube assembly or both; and
   a fill valve operatively engaged onto the fill tube assembly wherein the fill valve is in direct fluid communication with the reservoir and is capable of controlling fluid flow from the reservoir into the fill tube.

2. The fluid dispenser cartridge of claim 1, wherein said gas gating means comprises a substantially gas permeable material forming a portion of said fluid reservoir.

3. The fluid dispenser cartridge of claim 2, wherein said substantially gas permeable material is a sheet of polyethylene fiber.

4. The fluid dispenser cartridge of claim 2, wherein said substantially gas permeable material is a polytetrafluoroethylene membrane.

5. A fluid dispenser cartridge suitable for installation into an apparatus for dispensing predetermined volumes of fluid, the fluid dispenser cartridge comprising:
   a substantially rigid fluid reservoir having a fluid inlet and a fluid outlet, the fluid inlet suitable for introducing fluid into the substantially rigid fluid reservoir, the fluid outlet suitable for releasing fluid from the substantially rigid fluid reservoir;
   a fill tube assembly connected to said substantially rigid fluid reservoir at said fluid outlet such that fluid from said substantially rigid fluid reservoir can flow into said fill tube assembly, the fill tube assembly having a discharge port for dispensing fluid out of said fill tube assembly; and
   means for gating gas into or out of either said substantially rigid fluid reservoir or said fill tube assembly to substantially equalize pressure to that of the ambient environment during use of said cartridge in said apparatus; said gas gating means being disposed in either said substantially rigid fluid reservoir or said fill tube assembly or both; and
   a fill valve operatively engaged onto the fill tube assembly wherein the fill valve is in direct fluid communication with the reservoir and is capable of controlling fluid flow from the reservoir into the fill tube and a drain valve operatively engaged onto the fill tube assembly suitable for dispensing an aliquot into a receptacle.

6. The fluid dispenser cartridge of claim 5, wherein said gas gating means comprises a vent filter.

7. The fluid dispenser cartridge of claim 5, wherein said gas gating means comprises a pressure release valve.

8. The fluid dispenser cartridge of claim 5, wherein said gas gating means comprises a substantially gas permeable material forming a portion of said substantially rigid fluid reservoir.

9. The fluid dispenser cartridge of claim 8, wherein said substantially gas permeable material is a sheet of polyethylene fiber.

10. The fluid dispenser cartridge of claim 8, wherein said substantially gas permeable material is a polytetrafluoroethylene membrane.

11. The fluid dispenser cartridge of claim 1, wherein the fill tube is a closed loop.

12. The fluid dispenser cartridge of claim 1, wherein the fill tube is a non-closed loop.

13. The fluid dispenser cartridge of claim 1, wherein the fill valve is controlled by a solenoid.

14. The fluid dispenser cartridge of claim 1, further comprising an optical sensor.

15. The fluid dispenser cartridge of claim 5, wherein the fill tube is a closed loop.

16. The fluid dispenser cartridge of claim 5, wherein the fill tube is a non-closed loop.

17. The fluid dispenser cartridge of claim 5, wherein the fill valve is controlled by a solenoid.

18. The fluid dispenser cartridge of claim 5, further comprising an optical sensor.

19. The fluid dispenser cartridge of claim 5, wherein the reservoir is made of a material chosen from include polyethylene terephthalate, high density polyethylene, polyvinyl chloride, polypropylene, polystyrene, metal and glass.

20. A fluid dispenser cartridge suitable for installation into an apparatus for dispensing predetermined volumes of fluid, the fluid dispenser cartridge comprising:
a fluid reservoir having a fluid inlet and a fluid outlet, the fluid inlet suitable for introducing fluid into the fluid reservoir, the: fluid outlet suitable for releasing fluid from the fluid reservoir,
a fluid supply line connected to the fluid inlet and a sterilization or clarification filter disposed in the fluid supply line;
a fill tube assembly connected to said fluid reservoir at said fluid outlet such that fluid from said fluid reservoir can flow into said fill tube assembly during use of said cartridge in said apparatus, the fill tube assembly having a discharge port for dispensing fluid out of said fill tube assembly; and
a gas gate chosen from a vent filter assemblage and a pressure activated valve said gas gate being disposed in either said fluid reservoir or said fill tube assembly or both; and
a fill valve operatively engaged onto the fill tube assembly wherein the fill valve is in direct fluid communication with the reservoir and is capable of controlling fluid flow from the reservoir into the fill tube.

21. A fluid dispenser cartridge suitable for installation into an apparatus for dispensing predetermined volumes of fluid, the fluid dispenser cartridge comprising:
a substantially rigid fluid reservoir having a fluid inlet and a fluid outlet, the fluid inlet suitable for introducing fluid into the substantially rigid fluid reservoir, the fluid outlet suitable for releasing fluid from the substantially rigid fluid reservoir;
a fill tube assembly connected to said substantially rigid fluid reservoir at said fluid outlet such that fluid from said substantially rigid fluid reservoir can flow into said fill tube assembly, the fill tube assembly having a discharge port for dispensing fluid out of said fill tube assembly; and
means for gating gas disposed within the fill tube assembly to substantially equalize pressure to that of the ambient environment during use of said cartridge in said apparatus; and
a fill valve operatively engaged onto the fill tube assembly wherein the fill valve is in direct fluid communication with the reservoir and is capable of controlling fluid flow from the reservoir into the fill tube and a drain valve operatively engaged onto the fill tube assembly suitable for dispensing an aliquot into a receptacle.

22. The fluid dispenser cartridge of claim 21 further comprising a gas gating means disposed in the fluid reservoir.

* * * * *